United States Patent [19]
Alden et al.

[11] Patent Number: 5,125,963
[45] Date of Patent: Jun. 30, 1992

[54] METALLURGICAL CONTROLLING METHOD

[75] Inventors: Lars E. M. Alden; Erik W. Persson; Erik W. Wendt, all of Lund, Sweden

[73] Assignee: Scandinavian Emission Technology Aktiebolag, Blatungevagen, Sweden

[21] Appl. No.: 772,115
[22] PCT Filed: Aug. 17, 1988
[86] PCT No.: PCT/SE88/00420
   § 371 Date: Mar. 17, 1989
   § 102(e) Date: Mar. 17, 1989
[87] PCT Pub. No.: WO89/01530
   PCT Pub. Date: Feb. 23, 1989

Related U.S. Application Data

[63] Continuation of Ser. No. 340,299, Mar. 17, 1989, abandoned.

[30] Foreign Application Priority Data

Aug. 20, 1987 [SE] Sweden .............. 8703233
Feb. 2, 1988 [SE] Sweden .............. 8800321

[51] Int. Cl.⁵ .............................. C21D 11/00
[52] U.S. Cl. ............................ 75/375; 75/384; 75/385; 75/644; 75/696; 75/561; 75/567
[58] Field of Search .......... 75/375, 384, 385, 644, 75/696, 561, 567

[56] References Cited

U.S. PATENT DOCUMENTS

| 3,513,307 | 5/1970 | Dudgeon | 75/75 |
| 4,008,075 | 2/1977 | Petersson | 75/696 |
| 4,345,746 | 8/1982 | Schleimer et al. | 75/375 |
| 4,425,160 | 1/1984 | Mehta et al. | 75/63 |
| 4,651,976 | 3/1987 | Arima et al. | 75/375 |

FOREIGN PATENT DOCUMENTS 255911  12/1985  Japan .................. 75/45

Primary Examiner—Melvyn J. Andrews
Attorney, Agent, or Firm—Brumbaugh, Graves, Donohue & Raymond

[57] ABSTRACT

The present invention relates to a method for monitoring and control of smeltmetallurgical processes, endothermic as well as exothermic ones, preferably pyrometallurgical processes, by means of optical spectrometry, whereby one first determines for each endothermic and exothermic smeltmetallurgical process and/or process step characteristic emissions or absorptions and identifies the atomic or molecular origin of the emissions/absorptions, that one during a running process records changes in the characteristic emissions/absorptions and relates these changes to the condition of the process and with reference hereto controls the process.

13 Claims, 5 Drawing Sheets

METALLURGICAL CONTROLLING METHOD

This application is a continuation of application Ser. No. 07/340,299, filed on Mar. 17, 1989.

DESCRIPTION

1. Technical Field

The present invention relates to a method for monitoring and controlling of smeltmetallurgical, endothermic and exothermic processes, particularly pyrometallurgical processes by means of optical spectroscopy.

The object of the present invention is to obtain a possibility to control different smeltmetallurgical, endothermic and exothermic processes, particularly pyrometallurgical processes by spectrophotometry in a simple and rational way thus making it possible to improve the yield of the processes in a qualitative and quantitative way.

2. Background of the Invention

In pyrometallurgy, such as copper production, lead production, and iron and steel production fire and flames are generally encountered. The visual observation of these flames has for a long time been used to judge if and when such a process is to be interrupted or the running mode to be changed in any other way. In doing so one has then more or less on a firm ground supposed, that the process has reached a certain stage, phase or temperature as the flames have changed their colour, or seemingly have changed their color.

In iron production certain quantitative methods of analysis are in use, whereas in the copper production on-line methods are not in use to the same extent. Particularly the copper converting process uses purely visual methods for process control. In particular during the slag blowing phase and the production of blister copper it is important that the process is interrupted at the correct moment. An incorrect blowing time leads to an impaired yield and difficulties during the continued process. An incorrect temperature leads to disturbances of the process possibly leading to a break down. One requirement is thus that the end point of e.g. the slag blowing stage has to be determined to within better than one minute.

Depending on the composition of the melt the flame present above the converter will look different, and thus it can not easily be determined visually, if, and when, the process is to be interrupted.

Thus there exists a considerably technical problem to be solved within the smeltmetallurgy, at endothermic and exothermic processes, and in that connection particularly within pyrometallurgy but also in plasma smelting and electric arc smelting.

DESCRIPTION OF THE PRESENT INVENTION

It has now surprisingly been shown possible to solve the above mentioned technical problems by means of the present invention which is characterized in that one first determines, for each endothermic and exothermic smeltmetallurgical process and/or process step, characteristic optical emissions or absorptions and identifies the atomic and/or molecular origin of the emissions/absorptions, that one during an ongoing process run registers changes in the characteristics of the emissions/absorptions and relates these changes to changes of the status of the process, and that one controls the process with reference hereto.

One calculates preferably the ratio between intensities of at least two emitting products and/or the intensities at least two different wave lengths of one emitting product.

Further characteristics are evident from the accompanying claims.

The invention will be described more in detail in the following with reference to the example below, which example is directed to a copper converting process, however, without restricting the invention thereto.

EXAMPLE

Spectrophotometric measurements of a copper converter flame were carried out using a modern optical system capable of measuring either a complete spectrum or part of a spectrum with a high resolution in a very short time period, typically 10 ms. A Jarrel-Ash model 1233 spectrometer containing three interchangeable gratings was used to disperse the incoming light. The gratings covered the spectral range 3200Å, 800Å, and 200Å (and had 150, 600, and 2400 grooves per mm). The measurements were carried out in the wave length range 200 to 800 nm, and more particularly in the range 400 to 650 nm. The resulting spectra were recorded on a PARC model 1421 detector with 1024 diodes placed in a row in the exit plane of the spectrometer. The detector included an image intensifier. A PARC model 1460 OMA (Optical Multichannel Analyser) console was used to display the data, and spectra were stored on floppy discs for further processing and evaluation. The system was used both for emission measurements, when the light from the converter flame was focused on the entrance slit of the spectrometer, and for absorption measurements when light from a Xe-lamp after having passed the flame was fed through an optical fibre to the entrance slit.

Figure 1:
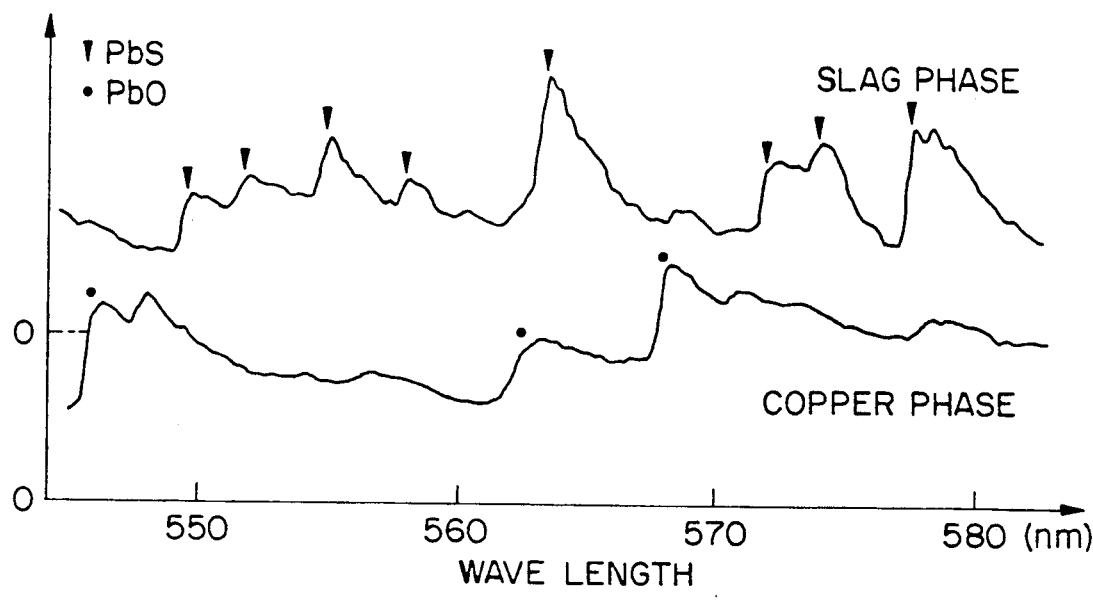
FIG. 1 shows parts of the spectra emitted for PbO and PbS during slag and copper making stages in a copper converting process.

It turned out that emission spectra from the slag and copper making stages were quite different. On the other hand spectral characteristics were reproducible from one process cycle to another. FIG. 1 shows parts of the spectra emitted during slag and copper making stages.

Figure 2:
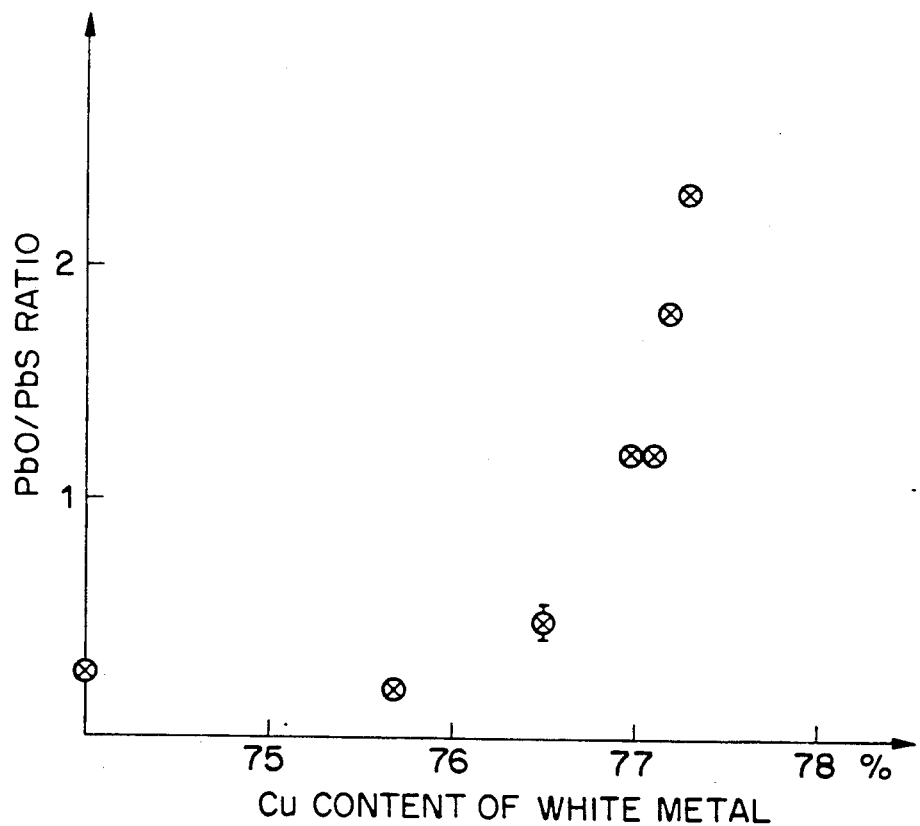
FIG. 2 shows a plot of PbO/PbS ratio vs. Cu content of white metal in a copper converting process.

The spectra consist of a continuous background caused by Planck radiation from particles in the flame and contributions from gaseous elements. It turned out that the dominating gaseous emitter during the slag phase was PbS while during copper making phase PbO dominated the emission spectrum. Close to the end of the slag phase one could observe that the emission spectrum started to change from a pure PbS spectrum to a mixture of a PbS and PbO spectra. A series of determinations were made in which the ratios between the intensity of certain PbO and PbS bands were recorded during the last minutes of the slag phase. FIG. 2 shows the end-point value of the ratio determined versus the copper content in the white metal (concentrated matte). When the ratio increases the copper content reaches an asymptotic value of 77.5 %. The Cu content of the white metal was determined using XRF (X-ray fluorescense) determinations on a sample taken after the interruption of the process. By means of the present measurements it could be determined that when PbO(g):PbS(g) approached 1 at the actual choice of wave lengths the slag blowing should be interrupted, however, preferably at a value of 0.2 to 0.5, whereat less amounts of metallic copper is formed.

Figure 5:
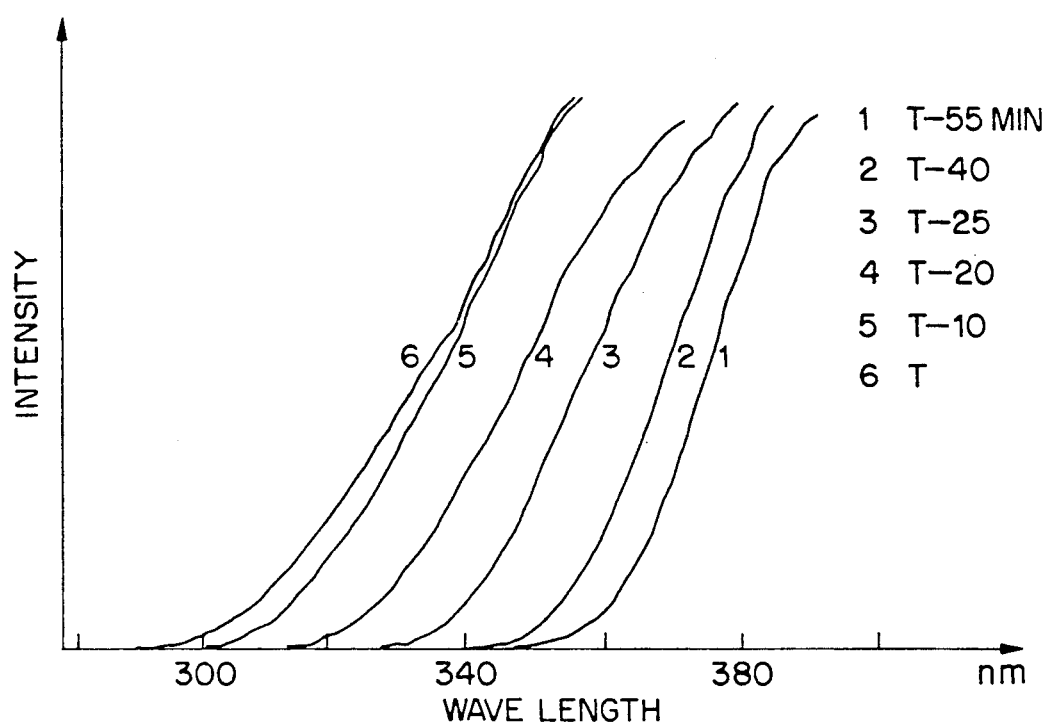
FIG. 5 shows a plot of intensity of $SO_2$ absorption vs. wavelength in a copper converting process.

Due to the high load of particles during slag phase it was possible to carry out absorption measurements only during the copper making phase. Preliminary observations showed a strong absorption at wave lengths shorter than 350 nm, which was in good agreement with laboratory measurements of $SO_2$ at 1200° C. When the end point is reached the concentration of $SO_2$ decreases and the transmission of light down to 350 nm can gradually be observed. A calculation of the ratio of the intensities at 320 nm and 350 nm was hereby used to determine the end point of the copper making phase. FIG. 5 shows the intensity of the $SO_2$ absorption versus the wave length at some different instants before the end point.

The theoretical composition of the gas phase in equilibrium with the matte and slag was calculated for comparison and as a guide in the analysis of the emission spectra recorded. In these calculations equilibrium conditions were assumed to be present during both slag and copper making phases. The assumption of equilibrium is not necessarily true for all elements but is likely to describe the major changes during the converting cycle. Necessary thermodynamic data were taken from a previous calculation of the copper converting process and assessment of slag data completed by data from thermodynamic tables. The calculation of the composition of the matte, white metal and slag phase in the converter process were carried out using the free energy minimizing program SOLGASMIX.

The metal-containing gaseous constituents which were considered in the calculations were PbS, Pb, PbO, Bi, Bi2, BiS, Zn, ZnS, As, $As_2$, $As_4$, AsS, AsO, $As_4S_4$, $As_4O_6$, Sb, $Sb_2$, $Sb_4$, SbO, and SbS.

Figure 3:
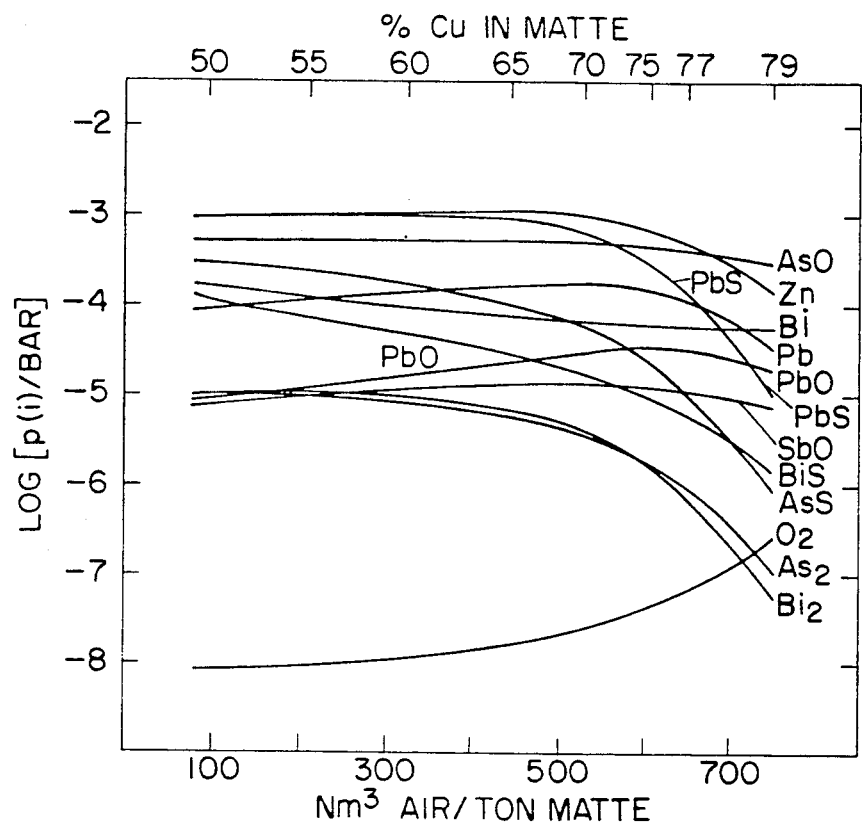
FIG. 3 shows the calculated partial pressure exceeding $10^{-6}$ bar during the slag production phase versus the amount of air injected per ton matte and the copper content of the matte in a copper converting process.

FIG. 3 shows the calculated partial pressure exceeding $10^{-6}$ bar during the slag production phase versus the amount of air injected per ton matte and the copper content of the matte. The calculated variation of the partial pressures of PbO(g) and PbS(g) is in good agreement with spectrometric measurements, and show a greater increase in the ratio p(PbO,g):p(PbS,g) at matte concentrations exceeding 75% of Cu.

Figure 4:
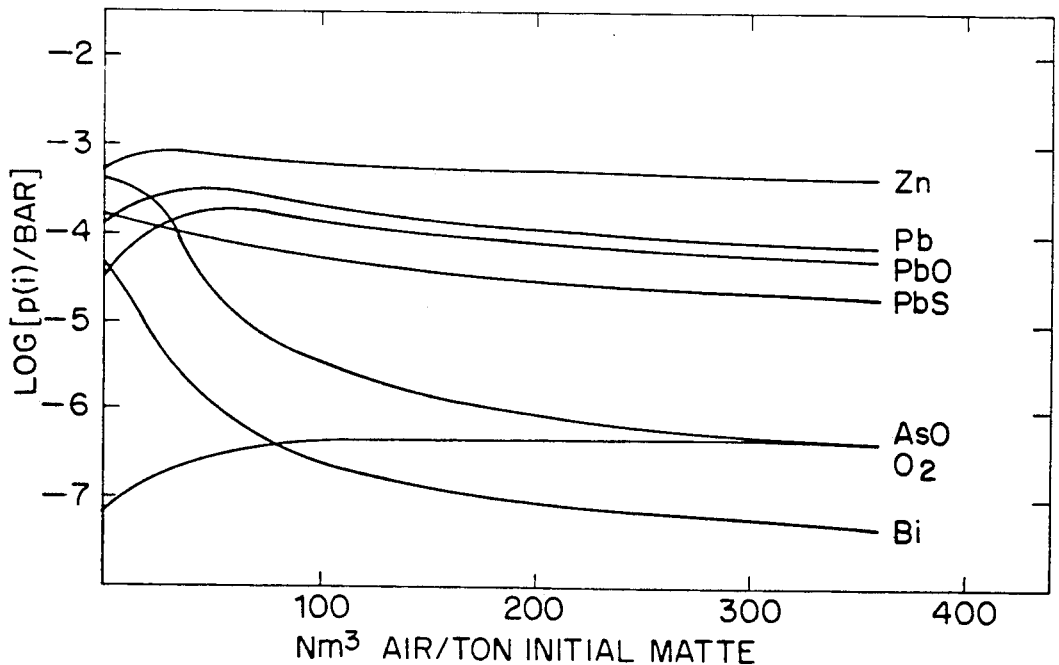
FIG. 4 shows calculated composition of the gas phase in the copper making stage versus the amount of air being injected per ton matte during the initial slag blowing stage.

FIG. 4 shows the calculated composition of the gas phase in the copper making stage versus the amount of air being injected per ton matte during the initial slag blowing stage. The white metal was supposed to contain 77.1% of Cu and 2% of the slag formed during the slag forming stage were supposed to be suspended in the white metal. From about 60 $Nm^3$ air per ton of initial matte metallic copper starts to form and from that point the p(PbO,g):p(PbS,g) ratio remains unchanged during the whole process with a value of about 2.6 in a quantitative agreement with the optical observation.

The calculated distribution in the gas phase is in good agreement with the values given in Table 1, below, with exceptions for Pb and Zn, for which the calculated values are lower than in practical operation. Consequently the partial pressures of lead and zinc compounds in the gas phase have to be higher than the values given in FIG. 3.

The determination of the end point of the slag forming stage and copper making stage in the converting process is today mainly dependent on skillful operators. Computer programs for the calculation of blowing time, addition of sand, and heat balances exist. However, the reliability of the calculated blowing time is dependent on the amount of Cu left in the converter from a previous cycle, the amount of slag in the matte added, the composition of scrap added and recirculated slag from different steps of the process, as well as the oxygen efficiency. All these parameters thus influence the process to a greater or lesser extent and thus have to be estimated by the operator. The calculated blowing time can thus be used as a coarse guide only to determine the end point and the final decision is today in the hands of the operator. However, as has been shown above the light emitted from the process can be used, after spectrometric determinations and analysis, to exactly determine the end point of the process steps, independent of the skill of the operators.

TABLE 1

|  | Cu | Zn | Pb | As | Sb | Bi | $SiO_2$ |
|---|---|---|---|---|---|---|---|
| Matte | 45.1 | 4.6 | 4.2 | 0.26 | 0.08 | 0.04 | — |
| Slag | 5.0 | 8.0 | 8.0 | 0.09 | 0.16 | — | 23.9 |
| White metal | 76.6 | 0.19 | 0.32 | 0.20 | 0.06 | 0.019 | — |
| Dust | — | 13 | 29 | 38 | 5 | 88 | — |

The values given are in % by weight for the composition of matte, slag and white metal in the actual plant.

By means of this new method the process can also be closed to a greater extent which leads to less emissions of sulphur dioxide through the ventilation system of the plant.

The invention is thus based on a technique where, in this case, the end point of the slag producing phase of a copper process can be determined by measurements of the intensity ratios between the emitted light from PbO(g) and PbS(g) whereby variations in the background due to disturbances are restricted, and disturbances from variations in the total lead content are restricted as long as spectra from lead compounds can be identified. The lead content in the white metal formed in the slag phase varied in the actual plant between 0.5 to 2 % by weight and even at lower concentrations the emitted light was strong enough to be detected. The variations of the silicon content of the slag influences the oxygen partial pressure and thus also the PbO:PbS ratio in the gas phase. These differences dependent on variations of the silicon content are small compared with the rapid increase of the PbO:PbS ratio at the end of the slag producing phase.

The utilization of the present method for an exact monitoring and control of the slag producing phase at a copper process leads to potentially great advantages as the number of over blows and to early interrupted slag blows are reduced to a minimum. Normally the copper content of the white metal is 76 to 77 % after the final blow. If this step is interrupted too early the blow has to be restarted after an analysis, which takes about 20 minutes to carry through. If on the other hand one drives the copper making stage with too low Cu content there exists a considerable risk for of the formation of magnetite and an increased risk of slag foaming with a great time loss as a consequence.

The exact monitoring and control of the copper content is also essential to optimize the removal of impurities to the slag phase during the slag stage. Several impurities such as Ni and Sb show an improved distribution to the slag phase at higher copper concentrations but if the blow continues above 78% of copper in the white metal metallic copper starts to form as indicated above, and this counteracts the elimination of impurities to the slag as the distribution of impurities between slag and metallic copper is more unfavorable than between slag and white metal.

It is not only the Cu concentrations which are of interest to control, but it is also possible to determine and control the release of halogenides which are known to form compounds with precious metals. The precious metals are a valuable constituent in the form of an impurity in the copper metal and these precious metals should not be evaporated in the form of gaseous molecules with a halogen.

Figure 9:
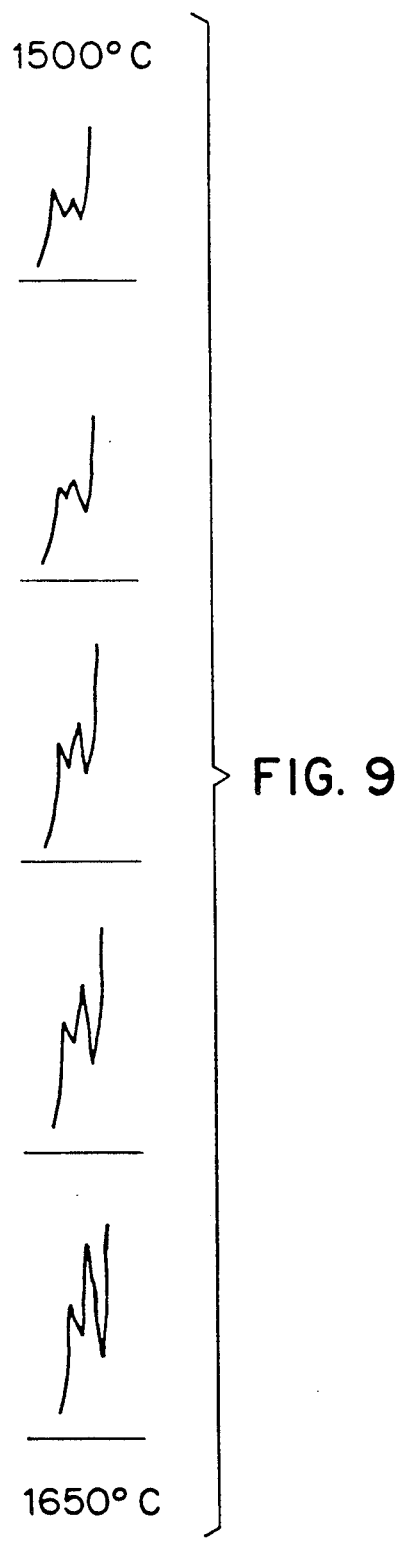
FIG. 9 shows the changes in relative intensities of two emissions of one product at various temperatures in an iron/steel production process.

In the same way the temperature can easily be followed in a process by recording and comparing the intensities in different emission/absorption bands from one and the same molecule and/or the width of an emission/absorption band from one and the same molecule. For example one can record and compare the intensities of the PbO bands in a copper process, and in an iron steel process different atomic Fe lines can be compared with each other. FIG. 9 shows the changes in relative intensities of two emissions of one product of an iron/steel process, where the intensities are recorded from 1500° C. (top), and to 1650° C. (bottom). Thus there is a gap of approximately 35° C. between each recording. As is evident from these recordings the temperature can be easily determined by re-cording and calculating the ratios between the two intensities.

The use of the present invention means that open converter processes can easily be closed and thereby it is possible to radically improve the environment in and around a smelter. Further by closing the process gas collecting systems do not need to be dimensioned for the large gas volumes necessary to handle when using an open converter to remove hazardous gases leaking to the environment but can be adopted to the amount of gas which is really produced in the process.

Figure 6:
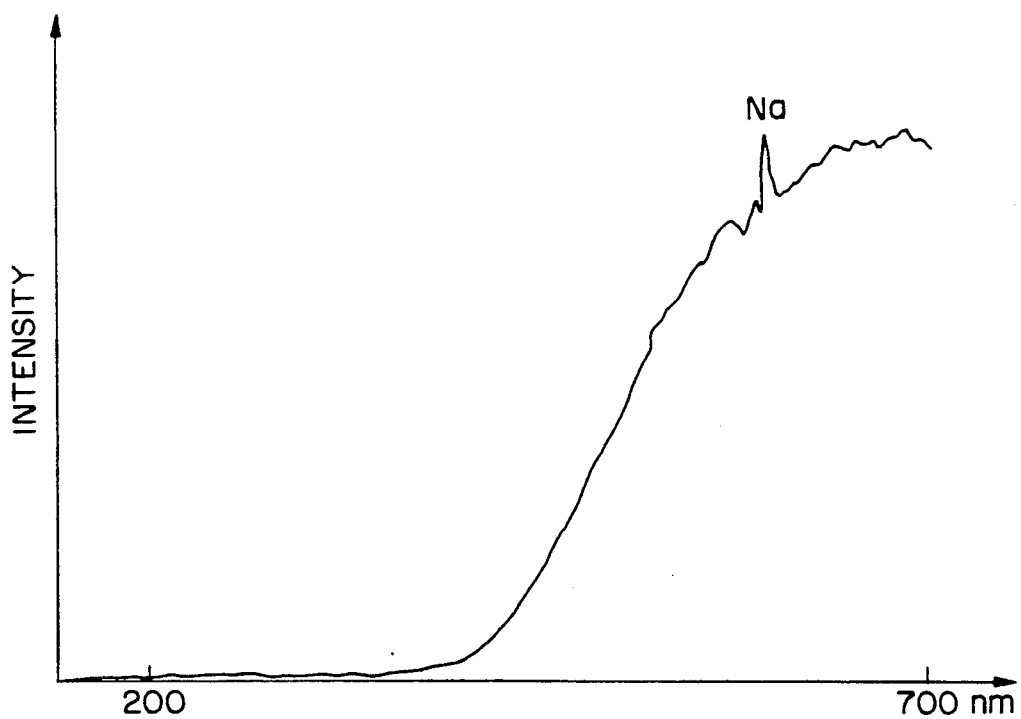
FIG. 6 shows an emitted spectrum from a converter flame in a small resolution in the interval 200-700 nm in a copper converting process.
Figure 7:
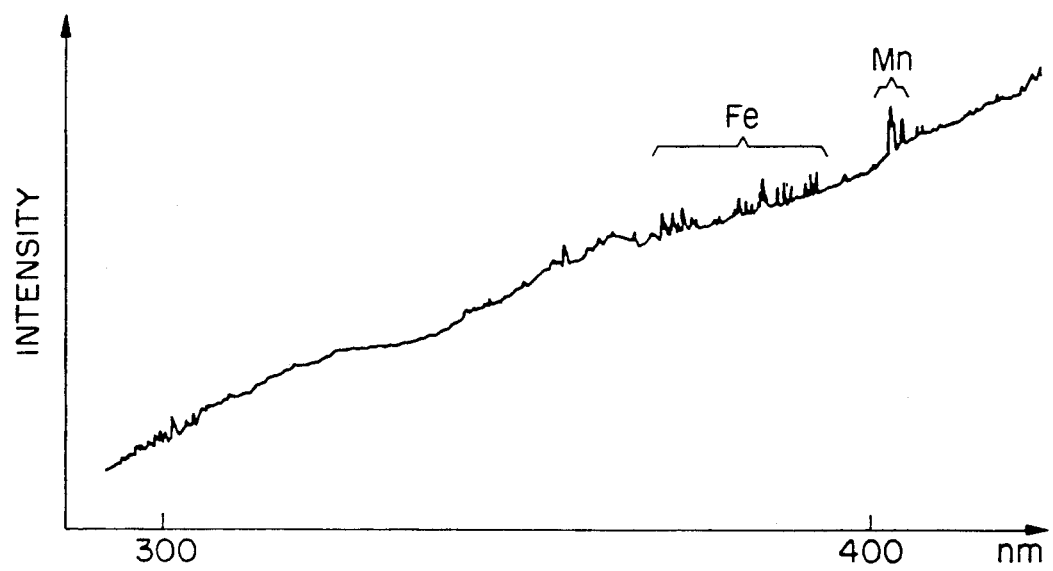
FIG. 7 shows a spectrum of a hot spot in the wave length interval 200-300 nm in a copper converting process.

In producing iron and steel one can, in the way described above, record and compare the intensities of different carbon compounds (CO, $CO_2$, CN—) or work with different atomic states in for example Fe, Mn, K, Na, etc. in order to determine the condition of the process. The measurement is carried out in the interval 260 to 600 nm, more preferably in the interval 300 to 400 nm. FIG. 6 shows the emitted spectrum from a converter flame in a small resolution in the interval 200 to 700 nm, and FIG. 7 shows a spectrum of the hot spot in the wave length interval 200 to 300 nm, in which spectrum the majority of the discrete structures come from atomic iron, but also atomic manganese, sodium, and potassium have been identified. Strong iron and manganese lines have been marked in FIG. 7. The recordings show that the ratio Fe/Mn changes during the blow in a converter, as well as the K/Fe ratio varies considerably.

During the production of alloy steel, stainless steel and other qualities, Ni, Cr, Mn, Mo, Al, MgO, CaO, are present in the smelt, and, in particular, FeSi is present during the reduction phase. Mn and Cr are present as compounds and can be easily determined.

In the same way as described above the temperature in a smelter can be determined accurately, and the elementary composition of the melt can be determined in order to reach a correct alloy point. It is important in a steel making process to reach the correct concentration of carbon at the correct temperature of the melt. This can easily be achieved by means of the present invention. One can also use the method for measuring the composition of the alloying metals of the iron. The elementary composition can be used to control the addition of alloying metals which has become more important because of the increasing use of scrap metal, the total composition of which is very uncertain.

Figure 8:
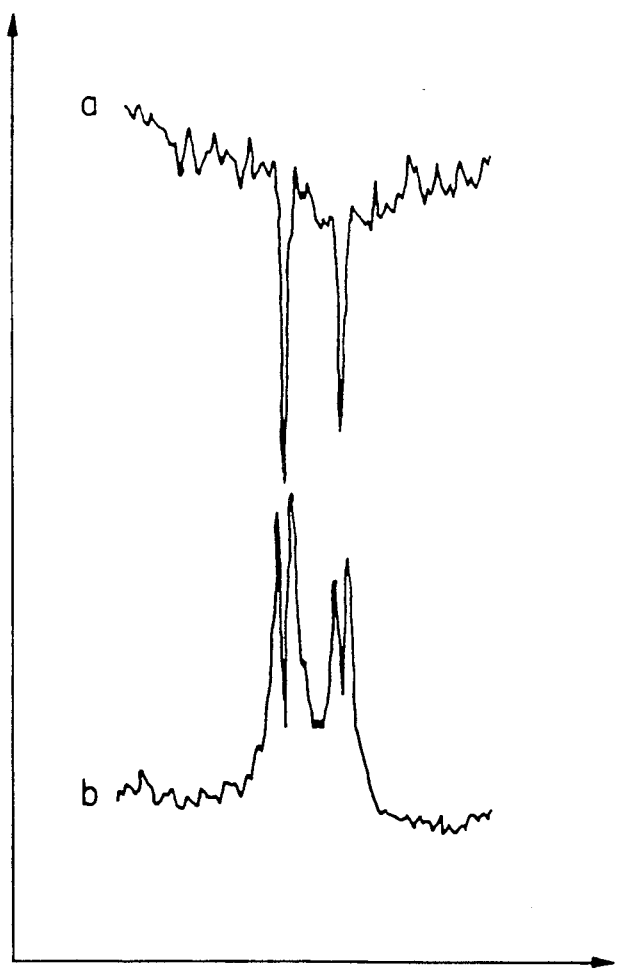
FIG. 8 shows a plot of sodium lines in absorption and emission in a copper converting process.

It is also very important to be able to monitor the status of the lining of a melting furnace so that the lining is not worn out and a penetration of the converter/furnace takes place, which can cause very high costs. The quality of the lining layer can easily be determined by monitoring through the oxygen lance the K, Na, and Al presence in the hot spot. Particularly monitoring of the emission/absorption of Na makes it possible to check the lining. The determination hereby involves a study of the intensity and shape of the absorption and emission lines of Na and K, particularly at 600, and 400 nm, respectively. Compare FIG. 8 in which graph a) shows the sodium lines in absorption only, and graph b) the lines as self-reversed emission lines.

At the production of lead the ratio PbO:PbS can of course be used as well as bands from impurities like Hg.

As evident from above impurities, but also a product to be produced but present in a characteristic intermediary form can be utilized for these recordings and comparisons for process control.

As indicated the method can use different measuring methods such as direct optical measurement using conventional optics, but also modern fibre optics whereby process control based on the conditions underneath a protecting and cooling slag layer is technically possible. A protecting and cooling slag layer may sometimes change the status of the atom or molecule on which a determination is based and thus it may be of utmost interest to follow the conditions at the actual reaction site. This situation is encountered for example, in a steel melt during oxygen blowing.

We claim:

1. A method using optical spectrometry for monitoring and control of a smelt-metallugical process having individual process stages and carried out in a converter, in which light is emitted and absorbed by atomic or molecular species formed during the process, comprising:
   (a) identifying the atomic or molecular origin of at least one atomic or molecular species formed during the process, selecting at least two wavelengths at which said at least one species formed during the process has a measurable intensity, and measuring the intensity and spectral distribution of light emission, light absorption or both of said at least one species corresponding to said at least two wavelengths at least periodically throughout the process within the converter, wherein the emission, absorption, or both is characteristic of the process, and recording these values at least momentarily;

(b) determining at least one ratio of the measured intensity of said at least one species at a minimum of two of said wavelengths;

(c) comparing the ratio or ratios thus determined to known values of the same ratios at various individual stages in the process;

(d) converting the results of this comparison to a signal for process control of the process; and (e) employing the signal as an input signal to means for varying process control parameters affecting the individual process stages.

2. A method according to claim 1, wherein the process controlled is copper conversion, the species formed during the process include PbO and PbS, and the emissions measured are those from PbO and PbS within the wavelength range 200 to 800 nm, the comparison with known values signaling the end of the slag production phase.

3. A method according to claim 2, wherein the wavelength range is 400 to 650 nm.

4. A method according to claim 1, wherein the process controlled is copper production, the species formed during the process include halogenides of precious metals, and the wavelengths selected are indicative of halogenides of precious metals present in the gas phase.

5. A method according to claim 1, wherein the process controlled is copper conversion, the species formed during the process include $SO_2$, and the light absorptions measured are those from $SO_2$ within the wavelength range 300 to 400 nm.

6. A method according to claim 1, wherein the process controlled is lead production, the species formed during the process include PbO and PbS, and the emissions measured are those from PbO and PbS.

7. A method according to claim 1, wherein the process controlled is iron and steel production, the species produced therein include carbon compounds and free atoms selected from the group consisting of Fe, Mn, K, and Na or a combination thereof, and the emissions measured are those from compounds or free atoms selected from the group consisting of Fe, Mn, K, and Na, or a combination thereof, within the wavelength range 200 to 800 nm.

8. A method according to claim 1, wherein the process controlled is iron and steel production, and measurements taken with respect to the alloying metals of an iron melt are converted to a process control signal and employed to monitor and control the addition of alloying metals and carbon to the process.

9. A method according to claim 7, wherein the process controlled is iron and steel production, and measurements taken with respect to the alloying metals of an iron melt are converted to a process control signal and employed to monitor and control the addition of alloying metals and carbon to the process.

10. A method according to claim 1, wherein the process produces species including K, Na, and Al, and is monitored by determining the light emission, light absorption, or both of one or more elements selected from the group consisting of K, Na, and Al.

11. A method according to claim 10, wherein the light emission, light absorption or both is measured for Na at 600 nm and for K at 400 nm.

12. A method according to claim 1, wherein measurements are spectrophotometrically made immediately above the melt.

13. A method according to claim 1, wherein measurements are spectrophotometrically made by means of a lance introduced into the melt, the lance comprising fiber optical measurement means.

* * * * *

UNITED STATES PATENT AND TRADEMARK OFFICE
CERTIFICATE OF CORRECTION

PATENT NO. : 5,125,963

DATED : June 30, 1992

INVENTOR(S) : ALDEN ET AL

It is certified that error appears in the above-identified patent and that said Letters Patent is hereby corrected as shown below:

On title page, item [73] "Blatungevagen" should read --Lund--;

Col. 2, line 30, "at" should read --at at--;

Col. 5, line 11, "for of" should read --of--;

Title page, item [56] "U.S. PATENT DOCUMENTS" insert the following:

| | | | |
|---|---|---|---|
| 4,251,269 | 02/17/81 | Hoshi et al. | 75/45 |
| 4,296,086 | 10/20/81 | Whitehead | 423/392 |
| 4,222,506 | 09/16/80 | Sakashita et al. | 222/600 |

Signed and Sealed this

Twelfth Day of April, 1994

BRUCE LEHMAN

*Commissioner of Patents and Trademarks*

*Attest:*

*Attesting Officer*